United States Patent
Glinn et al.

(10) Patent No.: US 12,044,668 B1
(45) Date of Patent: Jul. 23, 2024

(54) CANNABIS POTENCY TESTING METHOD

(71) Applicants: Michele Glinn, Lansing, MI (US); Gregoire P. Michaud, Lansing, MI (US); Todd W. Welch, Lansing, MI (US)

(72) Inventors: Michele Glinn, Lansing, MI (US); Gregoire P. Michaud, Lansing, MI (US); Todd W. Welch, Lansing, MI (US)

( * ) Notice: Subject to any disclaimer, the term of this patent is extended or adjusted under 35 U.S.C. 154(b) by 0 days.

(21) Appl. No.: 18/369,920

(22) Filed: Sep. 19, 2023

Related U.S. Application Data

(63) Continuation of application No. 18/196,734, filed on May 12, 2023, now Pat. No. 11,782,040.

(51) Int. Cl.
| | |
|---|---|
| *G01N 1/28* | (2006.01) |
| *G01N 30/72* | (2006.01) |
| *G01N 33/00* | (2006.01) |
| G01N 30/02 | (2006.01) |

(52) U.S. Cl.
CPC ......... *G01N 33/0098* (2013.01); *G01N 1/286* (2013.01); *G01N 30/7233* (2013.01); *G01N 2001/2866* (2013.01); *G01N 2030/027* (2013.01)

(58) Field of Classification Search
CPC ............... G01N 33/0098; G01N 1/286; G01N 30/7233; G01N 2001/2866; G01N 2030/027
See application file for complete search history.

(56) References Cited

U.S. PATENT DOCUMENTS

| | | | |
|---|---|---|---|
| 2005/0258285 A1* | 11/2005 | McCambridge | A61B 10/0096 241/2 |
| 2008/0202259 A1* | 8/2008 | Stewart | G01N 1/286 73/863 |
| 2009/0061522 A1* | 3/2009 | Collins, Sr. | G01N 33/6839 436/21 |
| 2014/0271940 A1* | 9/2014 | Wurzer | A61K 36/185 424/725 |
| 2015/0017670 A1* | 1/2015 | Quinlan | B01L 3/5635 435/288.4 |
| 2015/0056712 A1* | 2/2015 | Powell | G01N 33/15 436/111 |
| 2016/0299119 A1* | 10/2016 | Laukkanen | C12Q 1/40 |
| 2016/0330976 A1* | 11/2016 | Mitter | G01N 33/0098 |
| 2018/0143212 A1* | 5/2018 | Giese | A61K 36/185 |

(Continued)

*Primary Examiner* — David J Bolduc

(57) ABSTRACT

The cannabis potency testing method quantitates cannabinoids with UV detection. The cannabis potency testing method may be used for analysis of cannabinoids in plant material/flower form, or in some embodiments, other forms, such as gummies. The cannabis potency testing method includes cannabis plant samples that may be extracted and diluted in methanol then analyzed by, for example, a high-performance liquid chromatography (HPLC) system in tandem with a Diode Array Detector (DAD). This method may utilize cannabis plant material, one or more grinding spheres, a container, and a grinder apparatus. The cannabis potency testing method allows determination of high- and low-level cannabinoids in a single injection, and meets or exceeds AOAC standards for analysis of cannabinoids in dried plant materials, concentrates, and edibles.

19 Claims, 6 Drawing Sheets

(56) References Cited

U.S. PATENT DOCUMENTS

| | | | |
|---|---|---|---|
| 2018/0284145 A1* | 10/2018 | Giese | G01N 33/948 |
| 2019/0033185 A1* | 1/2019 | Dombrowski | G01N 1/286 |
| 2019/0079063 A1* | 3/2019 | Gilboa-Geffen | G01N 33/58 |
| 2020/0008431 A1* | 1/2020 | Mitter | C12N 1/20 |
| 2020/0140341 A1* | 5/2020 | Garbe-Schoenberg | G01N 1/44 |
| 2020/0150005 A1* | 5/2020 | Slutter | C12M 47/06 |
| 2020/0271552 A1* | 8/2020 | Smith | G01N 1/286 |
| 2021/0055188 A1* | 2/2021 | Iwamoto | G01N 33/6854 |
| 2021/0238580 A1* | 8/2021 | O'Neil | G01N 1/286 |

* cited by examiner

CANNABIS POTENCY TESTING METHOD

CROSS-REFERENCE TO RELATED APPLICATIONS

This application is a continuation of U.S. Non-Provisional patent application Ser. No. 18/196,734 filed on May 12, 2023, which is incorporated herein by reference.

TECHNICAL FIELD

The present disclosure relates to a method of analyzing potency in cannabis. More particularly, the present disclosure relates to a method for consistent and accurate cannabinoid analysis.

BACKGROUND

Cannabis has been utilized in the United States for centuries. Some of these uses have included production of clothing and ropes via hemp. Cannabis also became popular centuries ago as an ingredient in numerous medicinal products. Moving forward in history, Congress passed acts in the early 1900s to criminalize the production and possession of cannabis. Not until the 1960s did feelings toward cannabis change. In the US today, many states have legalized the use of cannabis for medical as well as recreational use.

Due to the legalization of cannabis in states across the country, state governments have had to regulate cannabis within their states. These regulations often involve various rules as to potency and contaminant (e.g., pesticides and metal) levels in cannabis. Because of various state regulations, producers and manufacturers of cannabis products typically must disclose to the customer the cannabinoid content and levels in cannabis products. Thus, prior to cannabis being sold in a state it must meet certain testing requirements. In particular, many states must fall within potency parameters set by the state government.

Potency testing, or cannabinoid analysis, may vary from lab to lab, with many testing procedures being inaccurate and lacking repeatability. When potency testing is inaccurate, harm can be caused to a user when levels are too high, leading to hospitalization. Potency testing can be extremely difficult to perform accurately because of the many forms cannabis takes, such as flowers, candies, oils, and baked goods. As such, it is imperative to have precise potency testing for recreational users and especially for medical cannabis users, whether the patient's immune system is compromised or not.

Accordingly, there is a need for a potency testing method that is accurate, repeatable, and reproducible. The present invention seeks to solve these and other problems.

SUMMARY OF EXAMPLE EMBODIMENTS

In one embodiment, a cannabis potency testing method includes preparing calibrators and QC samples with cannabinoid compounds prior to testing cannabis plant materials.

In one embodiment, a method of preparing cannabis plant material comprises including a range of 0.5 to 1.0 gram of homogenized cannabis plant material. Homogenization is achieved by placing a composite sample with one or more grinding spheres into a first container. The first container and the composite sample are agitated in a grinder apparatus for a first grinding. After the first grinding, the grinder apparatus is left idle to allow any friction-generated heat to dissipate. The composite sample in the first container is then ground in an additional, second grinding. After the second grinding, the composite sample is inspected and should be a powder substance. If a powder substance is not produced after the second grinding, then additional grinding may be performed under a fine powder substance is produced. The powder substance may be scraped from an inner surface, the sides, bottom, and top, of the first container and mixed with a resting portion so as to ensure a homogenous sample. Remove and weigh the grinding spheres from the first container. In some embodiments, up to two of the grinding spheres are removed from the first container. The grinding spheres should be partly or completely coated in plant material residue. The grinding spheres are placed in a conical vial with a predetermined amount of the powder substance. Once the powder substance is placed in the conical vial, HPLC-grade methanol is then added to the conical vial under a fume hood and vortexed. After the conical vial is done, the grinding spheres are removed from the conical vial using a removal device, such as tweezers, or a similar tool, and visually inspected. If the grinding spheres are not completely clean, then return to the conical vial and vortex for additional time. Lastly, the grinding spheres are weighed to determine the final weight of the extracted test portion.

In one embodiment, a method of diluting the composite sample includes placing supernatant into a first LC autosampler vial holding Methanol (MeOH) to undergo a 10-fold dilution. The 10-fold dilution sample is vortexed so as to produce a mixed dilution. A portion of the mixed dilution is transferred into a second LC autosampler vial containing Methanol (MeOH) to produce a 100-fold dilution of the sample. The second vial containing the 100×-diluted sample is inserted into a sample rack and placed into an autosampler carousel compartment at a preset temperature for injection into a previously calibrated High-Performance Liquid Chromatography with Diode-Array Detection (HPLC-DAD). Weights of the individual samples are entered into the HPLC-DAD analytical sequence. A data processing program then uses the weights entered to calculate results in mg/g and percent for individual samples. Raw results (not adjusted for sample weight) that are above or below the calibration curve cannot be calculated with precision. Accordingly, the analysis should be diluted and reinjected or repeated with more or less sample as appropriate to confirm the numerical value.

DETAILED DESCRIPTION OF EXAMPLE EMBODIMENTS

Figure 1:
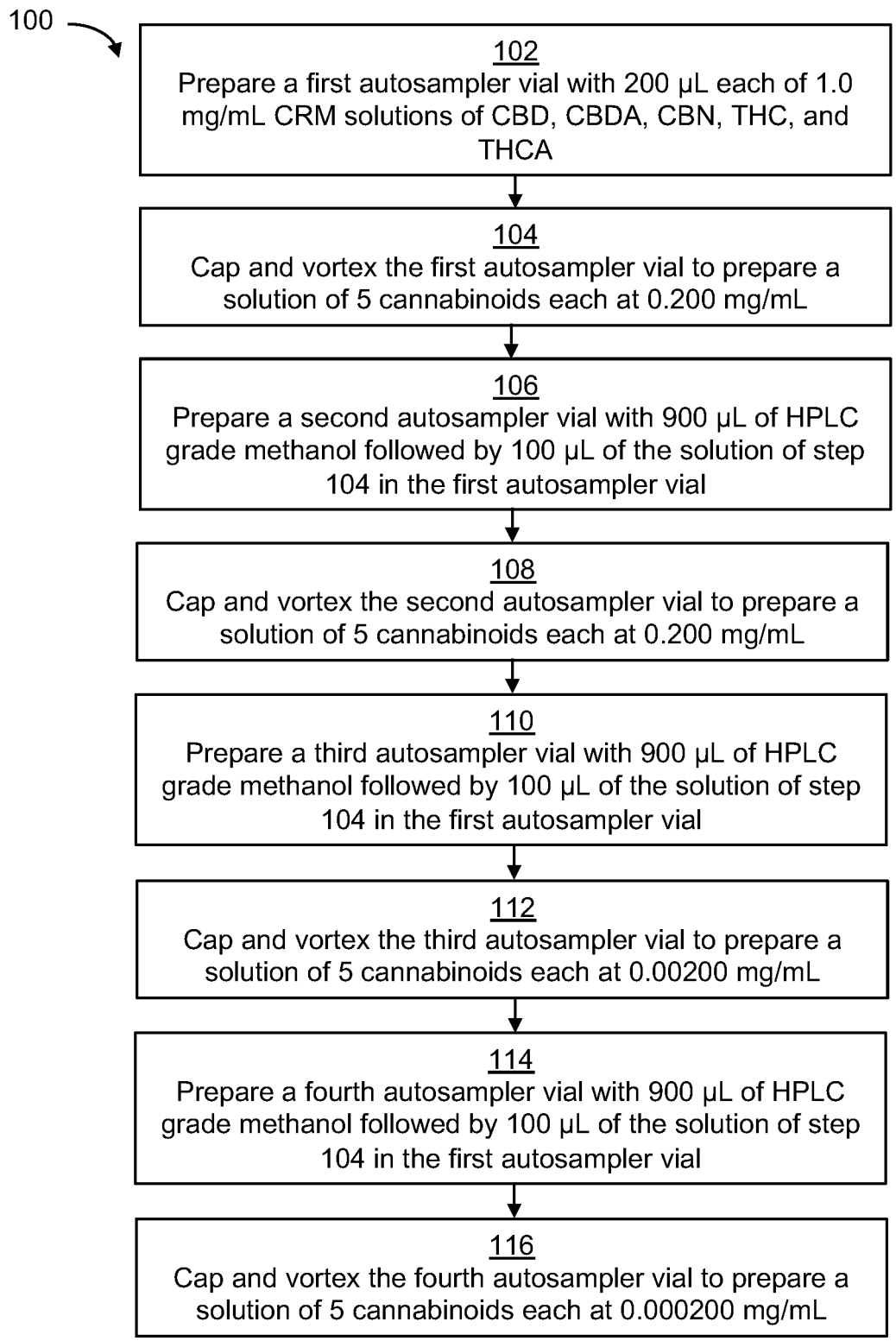
FIG. 1 illustrates a flowchart of a cannabis potency testing method.

While embodiments of the present disclosure may be subject to various modifications and alternative forms, specific embodiments have been shown by way of example in the drawings and will be described in detail herein. However, the present disclosure is not intended to be limited to the particular features, forms, components, etc. disclosed. Rather, the present disclosure will cover all modifications, equivalents, and alternatives falling within the scope of the present disclosure.

Reference to the invention, the present disclosure, or the like are not intended to restrict or limit the invention, the present disclosure, or the like to exact features or steps of any one or more of the exemplary embodiments disclosed herein. References to "one embodiment," "an embodiment," "alternate embodiments," "some embodiments," and the like, may indicate that the embodiment(s) so described may include a particular feature, structure, or characteristic, but not every embodiment necessarily includes the particular feature, structure, or characteristic.

Any arrangements herein are meant to be illustrative and do not limit the invention's scope. Although specific terms are employed herein, they are used in a generic and descriptive sense only and not for purposes of limitation. Unless otherwise defined herein, such terms are intended to be given their ordinary meaning not inconsistent with that applicable in the relevant industry and without restriction to any specific embodiment hereinafter described.

It will be understood that the steps of any such processes or methods are not limited to being carried out in any particular sequence, arrangement, or with any particular graphics or interface. In fact, the steps of the disclosed processes or methods generally may be carried out in various, different sequences and arrangements while still being in the scope of the present invention. Certain terms are used herein, such as "comprising" and "including," and similar terms are meant to be "open" and not "closed" terms. These terms should be understood as, for example, "including, but not limited to."

As previously described, there is a need for a potency testing method that is accurate, repeatable, and reproducible. The present invention seeks to solve these and other problems.

Cannabis testing is an essential part of regulating the industry in each state. Where cannabis is legal, states have passed regulations that control the testing parameters and potency levels of cannabis. However, numerous labs in a single state may vary on testing procedures, which may lead to inaccurate results. Furthermore, many of the testing procedures, while they claim to accurately analyze cannabis samples for potency levels, have shortcomings that lead to, at times, cannabis products at dangerous potency levels for consumers.

The cannabis potency testing method described herein quantitates 15 separate cannabinoids with UV detection. This method may be used for analysis of cannabinoids in plant material/flower form, or in some embodiments, other forms, such as gummies. In some embodiments, the UV detection in the cannabis potency testing method may be at 228 nm, supplemented by 214 nm and 275 nm channels (for confirmation of neutral and acidic cannabinoids, respectively) with collection of full UV spectra from 200-400 nm for all analytes. The cannabis potency testing method includes cannabis plant samples that may be extracted and diluted in methanol then analyzed by, for example, a high-performance liquid chromatography system (e.g., a Thermo Vanquish UHPLC System) in tandem with a Diode Array Detector (DAD)). This method may utilize grinding spheres as described herein. Data collection and analysis for the cannabis potency testing method may be operated on software (e.g., Chromeleon CDS) on a computing device. Concentration results may be obtained for the plant extracts in mg/g and also converted to % based on mass or volume of the original sample for reporting. It will be appreciated that the cannabis potency testing method allows determination of high- and low-level cannabinoids in a single injection, and meets or exceeds AOAC standards for analysis of cannabinoids in dried plant materials, concentrates, and edibles.

In one embodiment, a cannabis potency testing method (hereinafter referred to as the "method") may be used to test for the presence of phytocannabinoids (i.e., cannabinoids that are naturally in a cannabis plant) found in plant material and/or extracts of Cannabis sativa and C. indica. The method may test for the presence and potency of at least the following phytocannabinoids: delta-9-tetrahydrocannabinol (THC), tetrahydrocannabinolic acid (THCA), cannabidiol (CBD), cannabidiolic acid (CBDA), cannabinol (CBN), delta-8 tetrahydrocannabinol (delta 8-THC), cannabigerol (CBG), cannabigerolic acid (CBGA), cannabichromene (CBC), cannabichromenic acid (CBCA), cannabidivarin (CBDV), cannabidivarinic acid (CBDVA), cannabicyclol (CBL), tetrahydrocannabivarin (THCV), and tetrahydrocannabivarinic acid (THCVA).

The method may utilize ultra-high-performance liquid chromatography (UHPLC) coupled with a Diode Array Detector (DAD) to analyze extracts from plant materials, concentrates, and infused products for the concentrations of the specified compounds. Further, the method may use any of the following instruments to perform the method: a Thermo Vanquish UHPLC System with VF-P10-A UHPLC pump and a Diode Array Detector (DAD) Lightpipe™ VH-D10, with a Restek sub-2 micron UHPLC column (Raptor ARC-18 LC Column 1.8 μm×3.0 mm), and an optional guard column with 0.2 micron frit. Chromatography supplies and equipment may be from known vendors in the art, such as ThermoFisher, Restek, or other vendors. Solvents used in method may be HPLC-grade solvents that are obtained from companies such as Fisher Chemical, Alfa Aesar, Acros or Millipore Sigma. While these instruments and supplies may be used to carry out the method, it will be understood that other types of instrumentation and supplies may be used to perform the steps of method as discussed herein without departing from the method.

Furthermore, it will be appreciated that all standard laboratory precautions are observed while performing method. Some of these precautions may include at least the following: use of personal protective equipment, gloves, and use of all solvents in a fume hood. It will also be appreciated that the safety procedures utilized in the method adhere to those described in AOAC Appendix B on laboratory safety.

The method further includes reference standards. The reference standards are used to determine qualitative data, quantitative data, and calibration standards. In some embodiments, reference standards may come from Cerilliant, Cayman Chemical, Restek, Absolute Standards, or other known companies in the industry. The following chart represents reference standards from Cerilliant for the 15 separate cannabinoids:

| Compound | Abbreviation | Concentration | Cerilliant # |
|---|---|---|---|
| Cannabichromene | CBC | 1.00 mg/mL | C-143-1ML |
| Cannabichromenic Acid | CBCA | 1.00 mg/mL | C-150-1ML |
| Cannabidiol | CBD | 1.00 mg/mL | C-045-1ML |
| Cannabidiolic Acid | CBDA | 1.00 mg/mL | C-144-1ML |
| Cannabidivarin | CBDV | 1.00 mg/mL | C-140-1ML |
| Cannabidivarinic Acid | CBDVA | 1.00 mg/mL | C-152-1ML |

| Compound | Abbreviation | Concentration | Cerilliant # |
|---|---|---|---|
| Cannabigerol | CBG | 1.00 mg/mL | C-141-1ML |
| Cannabigerolic Acid | CBGA | 1.00 mg/mL | C-142-1ML |
| Cannabicyclol | CBL | 1.00 mg/mL | C-154-1ML |
| Cannabinol | CBN | 1.00 mg/mL | C-046-1ML |
| Δ8-Tetrahydrocannabinol | Delta 8 THC | 1.00 mg/mL | T-032-1ML |
| Δ9-Tetrahydrocannabinol | THC | 1.00 mg/mL | T-005-1ML |
| Tetrahydrocannabinolic Acid | THCA | 1.00 mg/mL | T-093-1ML |
| Tetrahydrocannabivarin | THCV | 1.00 mg/mL | T-094-1ML |
| Tetrahydrocannabivarinic Acid | THCVA | 1.00 mg/mL | T-111-1ML |

The method may include a calibration concentration range that is between 0.2 to 200 parts per million (ppm). In some embodiments, the method may be configured so that test portions of 0.5 to 1.0 grams will be diluted 1500× and the expected cannabinoid values in the diluted sample will fall within this range. As such, the final values may then be calculated according to sample weight and dilution. However, it should be noted that if the values in the diluted sample fall above or below the calibration range of 0.2 to 200 ppm, the sample may be reanalyzed at a higher or lower dilution level in order to be within the desired range. Due to the parameters of method, at test portion sizes of 0.5 to 1.0 grams and a typical 1500× dilution, the limit of quantitation (LOQs) and analytical ranges fall within the requirements of AOAC SMPR 2017.002. In addition, if the presence of one or more compounds are being not tested for, these compounds may be omitted from the calibrator or control solution and an equivalent volume of methanol substituted.

As shown in FIG. 1, a method for preparing calibrators 100 includes calibrators that may be processed through four separate stages. Preparation and utilization of the calibrators may be as follows: (1) At step 102, 200 μL each of 1.0 mg/mL CRM solutions of CBD, CBDA, CBN, THC, and THCA are added to a first autosampler vial. At step 104, the first autosampler vial is then capped and vortexed to prepare a solution of 5 cannabinoids each at 0.200 mg/mL for calibrator 4. (2) Then at step 106, 900 μL of HPLC grade methanol is added to a second autosampler vial, followed by 100 μL of the calibrator above (Calibrator 4) in step 104. At step, 108, the second autosampler vial is capped and vortexed to prepare a solution of 5 cannabinoids each at 0.0200 mg/mL for calibrator 3. (3) At step 110, 900 μL of HPLC grade methanol is added to a third autosampler vial, followed by 100 μL of the calibrator above (Calibrator 4) in step 104. At step 112, the third autosampler vial is capped and vortexed to prepare a solution of 5 cannabinoids each at 0.00200 mg/mL for calibrator 2. (4) At step 114, 900 μL of HPLC grade methanol is added to a fourth autosampler vial, followed by 100 μL of the calibrator above (Calibrator 4) in step 104. At step 116, the fourth autosampler vial is capped and vortexed to prepare a solution of 5 cannabinoids each at 0.000200 mg/mL (Cal 1). The above compounds in calibrator 4 and step 104 may be substituted with 200 μL each of 1.0 mg/mL CRM solutions of CBG, CBGA, CBC, CBCA, and, Δ8-THC; or, in another embodiment, the compounds in calibrator 4 and step 104 may be substituted for 200 μL each of 1.0 mg/mL CRM solutions of CBDV, CBDVA, CBL, THCV, and THCVA. Then the same process may be performed. That is, calibrator 3, 2, and 1 may be performed.

While specific amounts are shown above, it will be understood that the amounts of methanal and compound content may vary in other embodiments without departing herefrom.

Figure 2:
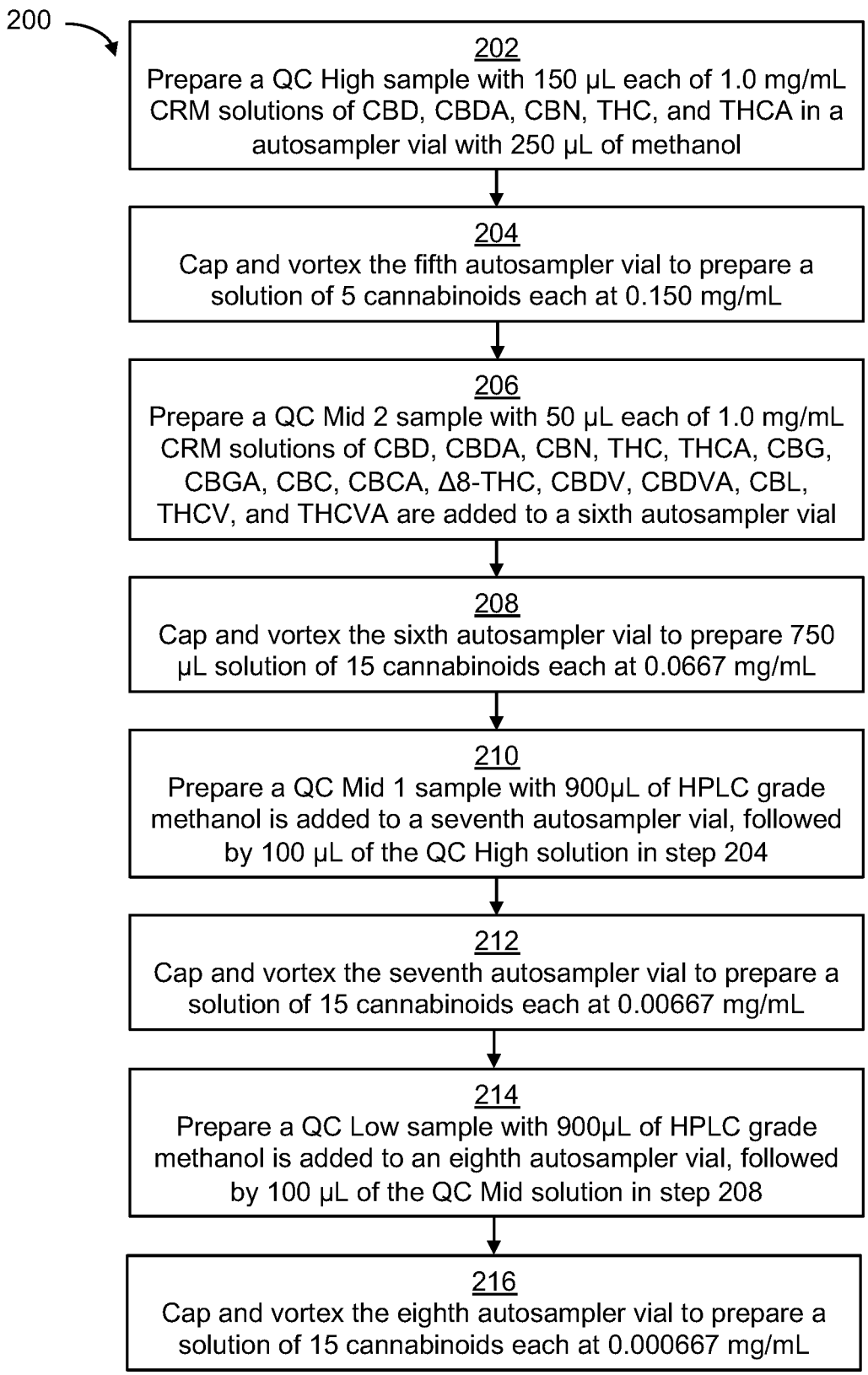
FIG. 2 illustrates a flowchart of a cannabis potency testing method.

After the above calibrators are set through the above procedures, preparations of QC low, mid, and high solutions are organized. FIG. 2 illustrates a QC preparation method 200 used in the method. Accordingly, at step 202, a QC high preparation may comprise 150 μL each of 1.0 mg/mL CRM solutions of CBD, CBDA, CBN, THC, and THCA are added to a fifth autosampler vial with 250 μL of methanol. At step 204, the fifth autosampler vial is capped and vortexed to prepare a solution of 5 cannabinoids each at 0.150 mg/mL (QC High). In some embodiments, the above CRM solution in QC High may be substituted with 150 μL each of 1.0 mg/mL CRM solutions of CBG, CBGA, CBC, CBCA, and Δ8-THC in step 202 (QC High—A); or substituted with 150 μL each of 1.0 mg/mL CRM solutions of CBDV, CBDVA, CBL, THCV, and THCVA in step 202 (QC High—B).

At step 206, a QC Mid 2 solution is prepared with 50 μL each of 1.0 mg/mL CRM solutions of CBD, CBDA, CBN, THC, THCA, CBG, CBGA, CBC, CBCA, Δ8-THC, CBDV, CBDVA, CBL, THCV, and THCVA are added to a sixth autosampler vial (e.g., a 1.5 mL autosampler vial). At step 208, the sixth autosampler vial is capped and vortexed to prepare 750 μL solution of 15 cannabinoids each at 0.0667 mg/mL (QC Mid 2).

At step 210, a QC Mid 1 solution is prepared with 900 μL of HPLC grade methanol is added to a seventh autosampler vial (e.g., a 1.5 mL autosampler vial) followed by 100 μL of the QC High solution above as found in step 204. At step 212, the seventh autosampler vial is capped and vortexed to prepare a solution of 15 cannabinoids each at 0.00667 mg/mL (QC Mid 1).

At step 214, a QC Low 900 μL of HPLC grade methanol is added to an eighth autosampler vial (e.g., a 1.5 mL autosampler vial) followed by 100 μL of the QC Mid solution above (QC Mid 2) as found in step 208. At step 216, the eighth autosampler vial is capped and vortexed to prepare a solution of 15 cannabinoids each at 0.000667 mg/mL (QC Low). While specific amounts are shown above, it will be understood that the amounts of methanal and cannabinoid compound content may vary in other embodiments without departing herefrom.

As an example, calibrator and QC concentrations may correspond to the following cannabinoid concentrations in samples of 0.3 or 1.0 grams with 1500 times dilution prepared as described below.

| Calibration Level | Calibrator mg/mL | 0.3 g 1500× Dilution Sample % | 1 g Sample 1500× Dilution Sample % |
|---|---|---|---|
| Cal 1 | 0.000200 | 0. | 0.0300 |
| QC Low | 0.000667 | 0.333 | 0. |
| Cal 2 | 0.00200 | 1.00 | 0.300 |
| QC Mid 1 | 0.00667 | 3.33 | 1.00 |
| Cal 3 | 0.0200 | 10.0 | 3.00 |
| QC Mid 2 | 0.0667 | 33.3 | 10.0 |
| QC High | 0.150 | 67.5 | 22.5 |
| Cal 4 | 0.200 | 100 | 30.0 |

Figure 3:
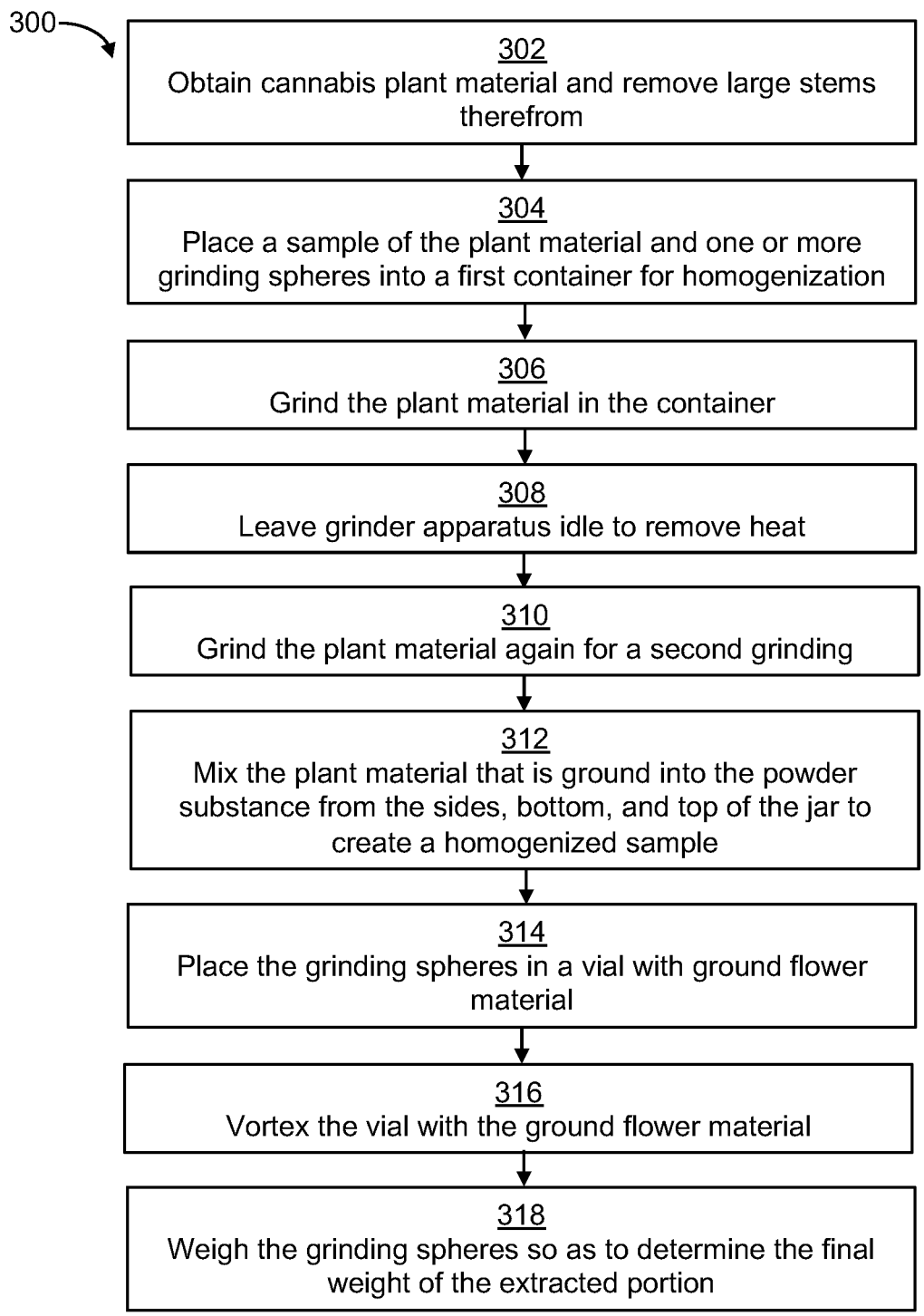
FIG. 3 illustrates a flowchart of a cannabis potency testing method.

In one embodiment, as shown in FIG. 3, a method of preparing cannabis plant material 300 in the method comprises a range of 0.5 to 1.0 gram of homogenized cannabis plant material, as discussed above. At step 302, prior to analysis, large stems are removed from the plant material. At step 304, homogenization is achieved by placing half of the composite sample (e.g., up to 60 grams of the composite sample) with one or more grinding spheres (e.g., 13 mm ceramic balls) into a first container (e.g., an amber container). While grinding spheres are discussed, it will be appreciated that other grindings members may be used. Other containers may be used herein such as a different color of container. In some embodiments, four grinding spheres may be placed in the first container. At step 306, the first container and the composite sample are agitated, in some embodiments, at first cycle rate (e.g., at or around 1650 cycles) per minute for a first time period (e.g., at or around 60 seconds) in a grinder apparatus (e.g., a SPEX Genogrinder) for a first grinding. While it is discussed that the first grinding is at about 1650 cycles per minute for 60 seconds in the grinder apparatus, it will be appreciated that, in an alternate embodiment, the first grinding may be at more or less than 1650 cycles per minute and more or less than 60 seconds in the grinder.

At step 308, after the first time period, the grinder apparatus is left idle for a second time period (e.g., at or around 30 seconds) or until any friction-generated heat dissipates. After this, in step 310, the composite sample in the first container is ground for a third time period (e.g., at or around 60 seconds), a second grinding. After the second grinding, the composite sample is inspected and should be a powder substance (e.g., a fine powder substance). However, if a fine powder substance is not produced after the second grinding, then a third grinding may be performed until the composite sample is a fine powder substance. At step 312, the fine powder substance may be scraped from an inner surface, the sides, bottom, and top, of the first container and mixed with a resting portion of the powder substance (i.e., composite sample) so as to ensure a homogenous sample. Remove and weigh up to two of the grinding spheres from the first container. In other embodiments, more or less than two grinding spheres may be removed for analysis. The grinding spheres should be partly or completely coated in plant material residue. Then, at step 314, the grinding spheres may be placed in a conical vial (e.g., a 50 mL conical screw-cap vial) with an additional 0.2-0.7 g of the powder substance, the ground flower material. Once the powder substance is placed in the conical vial, HPLC-grade methanol (e.g., 15.0 mL) is then added to the conical vial under a fume hood and vortexed at step 316. More particularly, the conical vial is then capped and placed in a vortexer (e.g., a Fisherbrand Multi-Tube Vortexer) for a fourth time period, (e.g., at or around 15 minutes) at or about 2000 rpm. After the conical vial is done in the vortexer, the grinding spheres are removed from the conical vial using a removal device, such as tweezers (e.g., disposable tweezers), or a similar tool, and visually inspected. If the grinding spheres are not completely clean (i.e., all ground material has been removed), then return to the conical vial and vortex for another period of time (e.g., 5 minutes). Lastly, at step 318, the grinding spheres are weighed to determine the final weight of the extracted test portion.

At times, there may be noncompliant samples. As such, if a noncompliant sample contains a small amount of flower material (e.g., one flower), it may be ground with a single grinding sphere in the conical vial (e.g., the screw-capped conical vial) to avoid losing sample to the sides of the container or damaging the container. With this example, methanol may be added directly to the vial after grinding is complete. It should also be noted that the amount of flower material may define the number of grinding spheres used in the method.

Figure 4:
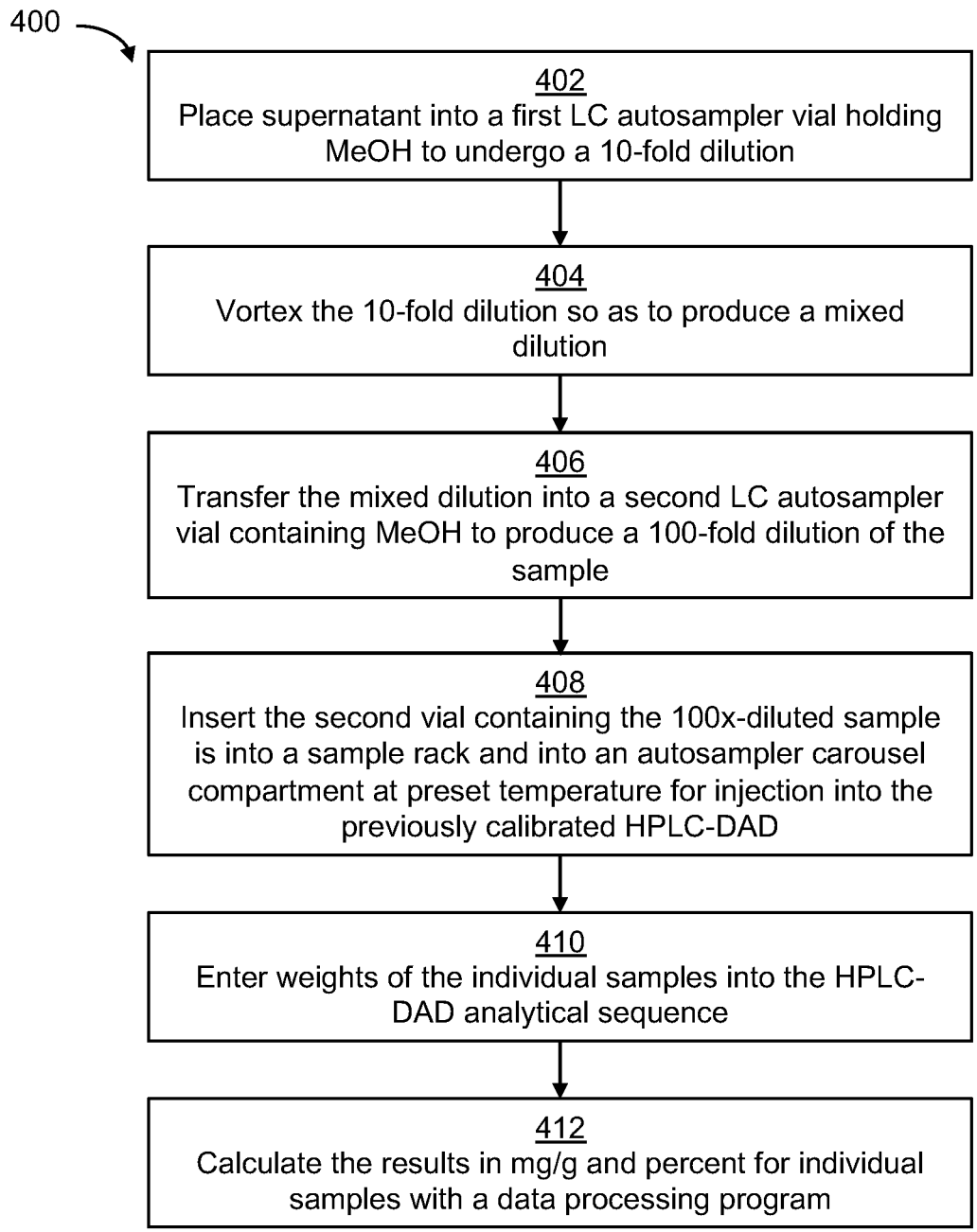
FIG. 4 illustrates a flowchart of a cannabis potency testing method.

After the methanol extraction is complete, as shown in FIG. 4, a method of diluting the sample 400 includes placing a first portion of supernatant (e.g., 100 μL) into a first LC autosampler vial holding a first amount of methanol (MeOH) (e.g., 900 μL) to undergo a 10-fold dilution at step 402. At step 404, the 10-fold dilution sample is vortexed so as to produce a mixed dilution. At step 406, a first portion of the mixed dilution (e.g., 100 μL) is transferred into a second LC autosampler vial containing a second amount of MeOH (e.g., 900 μL) to produce a 100-fold dilution of the sample. In an alternate embodiment, 10 mL of extract may be placed directly into a third LC vial with 990 mL of methanol. At step 408, the second vial containing the 100×-diluted sample is inserted into a sample rack and placed into an autosampler carousel compartment at a preset temperature (e.g., 10° C.) for injection into the previously calibrated HPLC-DAD. At step 410, weights of the individual samples are entered into the HPLC-DAD analytical sequence. A data processing program (e.g., Chromeleon) uses the weight entered to calculate results in mg/g and percent for individual samples at step 412. Raw results (not adjusted for sample weight) that are above or below the calibration curve cannot be calculated with precision. Accordingly, the analysis should be diluted and reinjected or repeated with more or less sample as appropriate to confirm the numerical value.

Below is a table describing one of the instruments used in the method.

| | |
|---|---|
| Column | Raptor ARC-18 LC Column 1.8 μm × 3.0 mm Cat.# 931421E |
| Guard Column | (optional): Precolumn filter with 0.2 μm frit, Restek 25811 or equivalent |
| Mobile Phase A | 5 mM ammonium formate/ 0.1% formic Acid in HPLC grade water |
| Mobile Phase B | 0.1% Formic Acid in HPLC grade Acetonitrile |
| Run Time | 6:00 minutes |
| Eluent | 25.0% mobile phase A/75.0% mobile phase B |
| Flow Rate | 1.000 mL/min |
| Column Temperature | 40.00° C. |
| Injection Volume | 2 μL |

Figure 5:
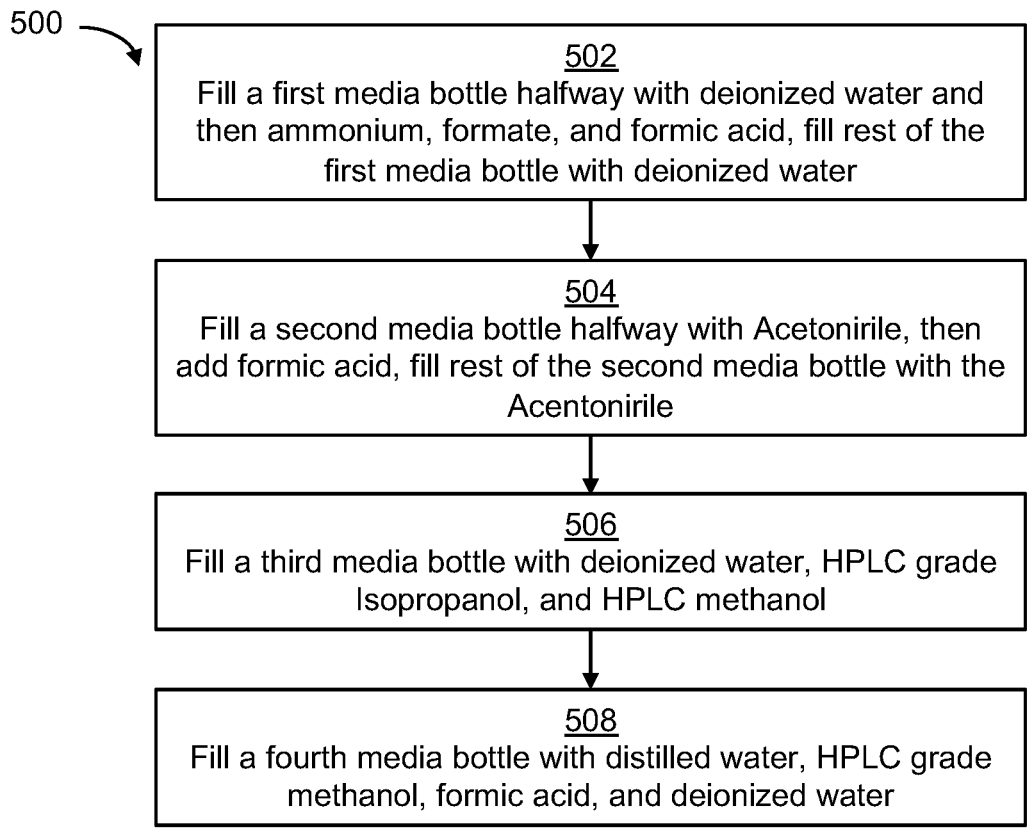
FIG. 5 illustrates a flowchart of a cannabis potency testing method.

As shown in FIG. 5, a method of preparing a liquid chromatography (LC) solution 500 comprises at step 502, filling a first 1 L media bottle halfway with deionized water. Add 315 mg ammonium formate and then add 1 mL formic acid (LCMS grade), then fill with deionized water to 1 L total volume (Mobile phase A). At step 504, fill a second 1 L media bottle halfway with HPLC grade Acetonitrile. 1.0 mL formic acid (LCMS grade), then fill with HPLC grade Acetonitrile to 1 L total volume (Mobile phase B). At step 506, fill a third 1 L media bottle with 300 mL each: Deionized water; HPLC grade Isopropanol and HPLC grade methanol (Needle Wash). At step 508, fill a fourth 1 L media bottle with approximately 500 ml distilled water and 100 mL HPLC-grade methanol. Add 1.0 mL Formic Acid (LCMS grade), then fill with Deionized water to 1 L total volume (Pump Seal Wash).

Figure 6:
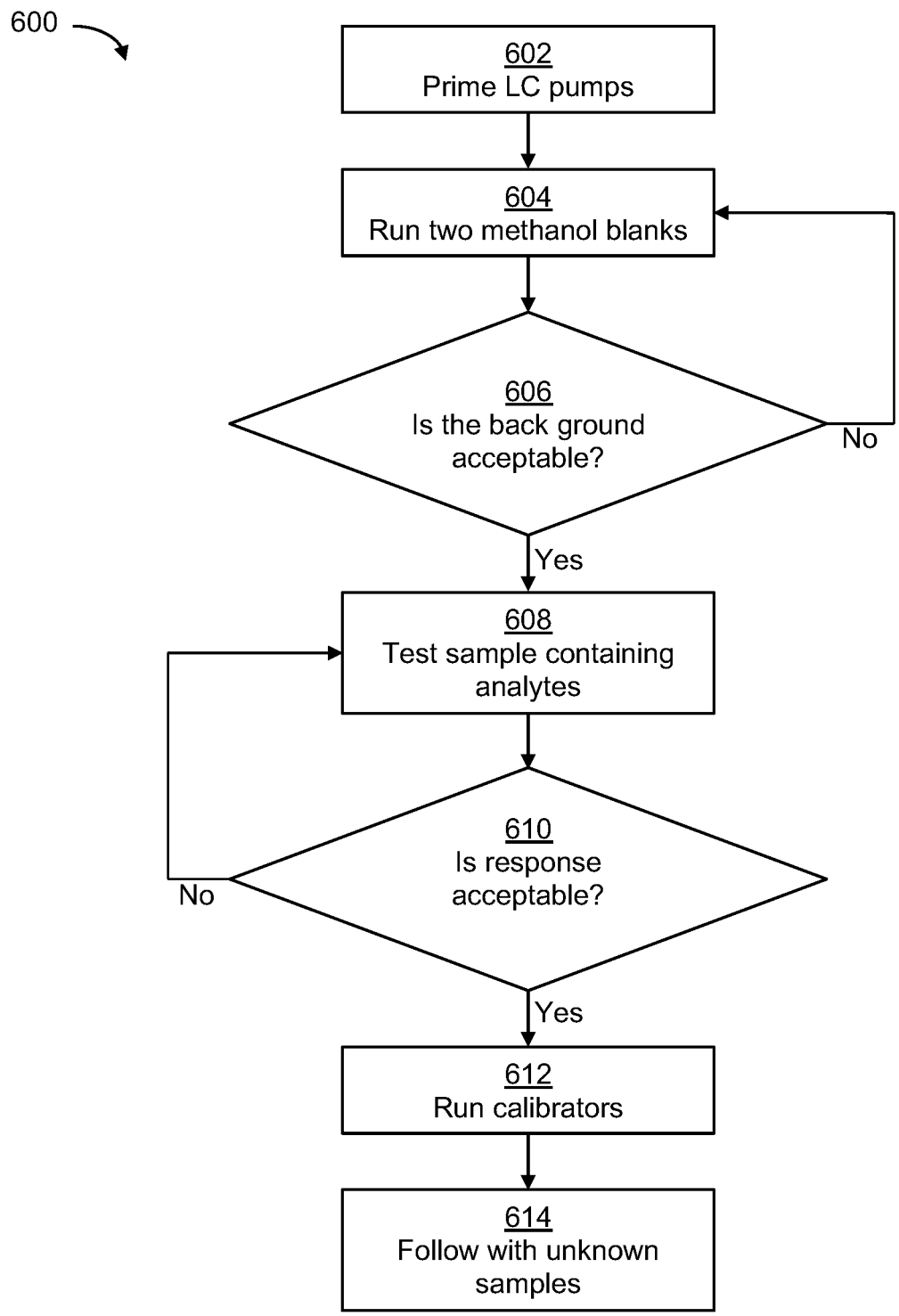
FIG. 6 illustrates a flowchart of a cannabis potency testing method.

As shown in FIG. 6, after the LC systems solutions are prepared, the user may then proceed with the following steps for a method of preparing the pump seal wash: (1) Prime the LC pumps at step 602; (2) Run two methanol blanks at step 604; (3) Determine if background is acceptable at step 606, acceptable background is defined as no spurious peaks at the retention times of interest and clear resolution of all analytes at the lowest calibrator level; (4) If acceptable background, proceed to step 608 and run: Test sample containing analytes of interest. If the test is not successful, return to step 604, or perform troubleshooting; (5) If response is acceptable at step 610, then run: Calibrators 1-4 at step 612. If response is not acceptable at step 610, then return to step 608; and (6) Follow with unknown samples at step 614.

Cannabis may vary from plant to plant and total cannabinoid content may reflect individual plant differences as well as intrinsic strain characteristics and cultivator skill. Accordingly, these variations and characteristics need to be factored into the process and analysis. Quantitative results may be monitored against previous results for the same strain and/or same customer ID when needed. Results of previous analyses can be viewed on a computing device comprising software (e.g., Sample Manager). As an example, these results may be viewed by customer and strain (i.e., Customer ID).

When tested samples show extreme variation or anomalous total THC levels, testing may be repeated to ensure the validity of the results as follows: (1) Flower samples with total THC results above about 27% may be repeated unless it has been seen that such high levels are typical for the strain analyzed. Trim samples with total THC results above about 20% may be repeated unless it has been seen that such high levels are typical for the strain analyzed. (2) Flower samples with total THC results below about 15% may be repeated unless it has been seen that these levels are typical for the strain analyzed, or the sample is known to be trim or the sample is known to be less potent for some other reason (i.e., plants were diseased). (3) Flower samples that are significantly different (>5%) from what has been previously reported for that strain from that customer may be visually evaluated and re-tested if necessary. (4) If multiple flower samples from the same batch, strain or source package are received from a customer and one of these are more than about 5% different from the rest, that sample may be visually evaluated and re-tested if no obvious reason for the disparity is observed.

To keep samples within acceptable parameters, quality control results may be evaluated for each run. Typically, multiple sets of QC samples are run in each batch. As an example, after the calibrators, bracketing every 20 unknown samples, and at the end of the run. It will be appreciated that all results should be within about 15% of the target values. If one sample per set is out, the analytical results may be accepted but a root cause analysis should be done as to why the control was out. If more than one sample per set is out, the results should not be accepted until a root cause analysis is done to determine where the analytical issue lies. All cannabinoid results may be reported "as is" and not corrected for moisture content.

Results after performing the steps of the method may be obtained in mg/g of extract and reported as such along with percent (%) in weight/weight or weight/volume as applicable. An example of reporting total THC and CBD to a state government may include the following formulas: 1) Total THC=(THCA*0.877)+d9-THC; or 2) Total CBD= (CBDA*0.877)+CBD. These formulas may vary based on state regulations.

In some embodiments, reference standards may be stored below 0° C. until used. In addition, calibrators and controls may also be stored below 0° C. until use and used within thirty days of preparation. Any LC system solutions, as discussed above, may be assigned an expiration date of one year from the date made and stored at room temperature and capped until used.

In one embodiment, the method may be performed with about 1.0 gram of infused product. For infused products, such as gummies, the individual items may be cut into small pieces. The pieces may then be combined into a container and mixed by shaking or inversion, and the amount needed selected from the combined, mixed pieces. About 1.0 gram of randomized product, or 1 mL of liquid products, is then weighed out on a calibrated analytical scale into a pre-tared vial (e.g., a 50 mL conical vial) placed in a beaker (e.g., a 250 ml beaker). For solid products, one grinding sphere (e.g., ceramic media ball) is added. Then 15 mL HPLC grade ethyl acetate, and 30 mL 10% formic acid in deionized water is added to the vial containing the infused product and placed onto a grinder apparatus (e.g., a SPEX Genogrinder) for, in some embodiments, 15 minutes agitation at 1350 cycles per minute. Liquid products with no grinding ball may be vortexed for 15 minutes on the multi-head vortexer. Following agitation, the vial is placed in a centrifuge (e.g., Thermo Scientific Legend XT Centrifuge or equivalent) for 10 minutes at 3000 RPM. As discussed above, once the centrifugation is complete, 100 µL of supernatant is placed into an LC autosampler vial holding 900 µL of MeOH to undergo a 10-fold dilution. The 10× dilution sample is vortexed and 100 µL of the mixed dilution is transferred into another LC autosampler vial containing 900 µL of MeOH to produce a 100-fold dilution of the sample. Alternatively, 10 L of the extract may be placed directly into an LC vial containing 990 L of MeOH.

In one embodiment, a third sample type comprises a concentrate. The concentrate may comprise liquid samples such as oils, or solid samples such as resins. The concentrates generally do not require homogenization, unlike sold solid samples that are typically powders or of a creamy consistency. The concentrates may be vortexed in methanol, without grinding media, and then diluted usually 100×. If the result is above or below the calibration curve, the sample should be repeated with a lower or higher dilution as above.

While certain amounts of solutions and dilutions above are at specific µL and mL, it will be understood that the amount of µL and mL may vary in each method without departing herefrom. Furthermore, the method described above allows for accurate, repeatable, and reproducible potency testing in cannabis plants. However, it should be noted that any result falling above or below the calibration curve should be repeated at a higher or lower dilution level to generate a numerically accurate result.

It will be understood that while various embodiments have been disclosed herein, other embodiments are contemplated. Further, systems and/or methods according to certain embodiments of the present disclosure may include, incorporate, or otherwise comprise properties or features described in other embodiments. Consequently, various features of certain embodiments can be compatible with, combined with, included in, and/or incorporated into other embodiments of the present disclosure. Therefore, disclosure of certain features or components relative to a specific embodiment of the present disclosure should not be construed as limiting the application or inclusion of said features or components to the specific embodiment unless stated. As such, other embodiments can also include said features, components, members, elements, parts, and/or portions without necessarily departing from the scope of the present disclosure.

The embodiments described herein are examples of the present disclosure. Accordingly, unless a feature or component is described as requiring another feature or component in combination therewith, any feature herein may be combined with any other feature of a same or different embodiment disclosed herein. Although only a few of the example embodiments have been described in detail herein, those skilled in the art will appreciate that modifications are possible without materially departing from the present disclosure described herein. Accordingly, all modifications may be included within the scope of this invention.

What is claimed is:

1. A cannabis potency testing method comprising:
performing a first grinding by agitating a container with a composite sample and one or more grinding members;
performing a second grinding by agitating the container with the composite sample;
creating a mixed powder substance from the composite sample;
removing the one or more grinding members from the container;
weighing the one or more grinding members;
placing the one or more grinding members, the mixed powder substance, and extraction solvent into a vial;
vortexing the vial with the one or more grinding members, the mixed powder substance, and the extraction solvent;
removing the one or more grinding members from the vial; and
weighing the one or more grinding members to determine the final weight of an extracted test portion.

2. The cannabis potency testing method of claim 1, further comprising resting the composite sample and one or more grinding members between the first grinding and the second grinding.

3. The cannabis potency testing method of claim 1, wherein the one or more grinding members comprise up to four grinding members.

4. The cannabis potency testing method of claim 1, wherein the one or more grinding members comprise grinding spheres.

5. The cannabis potency testing method of claim 1, wherein the container comprises a screw-capped lid.

6. The cannabis potency testing method of claim 1, wherein the first grinding is performed at a first cycle rate and at a first time period.

7. The cannabis potency testing method of claim 2, wherein the composite sample and one or more grinding members are rested for a second time period.

8. The cannabis potency testing method of claim 1, further comprising removing the one or more grinding members from the vial with a removal device.

9. The cannabis potency testing method of claim 1, further comprising creating a dilution appropriate to a calibration range.

10. The cannabis potency testing method of claim 1, further comprising removing supernatant from the vial.

11. The cannabis potency testing method of claim 1, further comprising placing a portion of a supernatant from the vial and a portion of the extraction solvent into an LC autosampler vial after one or more dilution steps.

12. A cannabis potency testing method comprising:
placing a composite sample with one or more grinding spheres into a container;
performing one or more grindings by agitating the container with the composite sample;
removing the one or more grinding spheres from the container where a powder substance formed from the composite sample;
weighing the one or more grinding spheres;
placing the one or more grinding spheres, the powder substance, and extraction solvent into a vial;
vortexing the vial with the one or more grinding spheres, the powder substance, and the extraction solvent;
removing the one or more grinding spheres from the vial;
weighing the one or more grinding spheres to determine the final weight of an extracted test portion;
removing supernatant from the vial;
diluting a first sample by an amount appropriate for an instrument calibration range by placing a portion of the supernatant and an amount of extraction solvent into an LC autosampler vial after one or more dilution steps.

13. The cannabis potency testing method of claim 12, further comprising placing the first, diluted sample into an autosampler carousel compartment at a preset temperature for injection into a previously calibrated high-performance liquid chromatography with diode-array detection (HPLC-DAD) device.

14. The cannabis potency testing method of claim 12, wherein the container comprises a screw-capped lid.

15. The cannabis potency testing method of claim 12, wherein the one or more grindings comprises a first grinding and a second grinding.

16. The cannabis potency testing method of claim 15, wherein the composite sample with the one or more grinding spheres rests for a period of time between the first grinding and the second grinding.

17. A cannabis potency testing method comprising:
performing one or more grindings by agitating a container with a composite sample;
resting the composite sample after a first grinding of the one or more grindings;
mixing a powder substance created from the composite sample after the one or more grindings to create a homogenous sample;
removing the one or more grinding members from the container;
weighing the one or more grinding members;
placing the one or more grinding members, the powder substance, and extraction solvent into a vial;
vortexing the vial with the one or more grinding members, the powder substance, and the extraction solvent;
removing the one or more grinding members from the vial;
weighing the one or more grinding members to determine the final weight of an extracted test portion;
removing supernatant from the vial; and
placing a portion of the supernatant into an LC autosampler vial after dilution with extraction solvent by an amount appropriate for an instrumentation calibration range to create a diluted sample.

18. The cannabis potency testing method of claim 17, further comprising placing the diluted sample into an autosampler carousel compartment at a preset temperature for injection into a previously calibrated high-performance liquid chromatography with diode-array detection (HPLC-DAD) device.

19. The cannabis potency testing method of claim 17, further comprising using a data processing program to calculate results.

* * * * *